United States Patent [19]

Chorvat et al.

[11] 4,399,279

[45] Aug. 16, 1983

[54] 4H-1,4-BENZOTHIAZINE DERIVATIVES AND INTERMEDIATES THERETO

[75] Inventors: Robert J. Chorvat, Arlington Heights; Bipinchandra N. Desai, Vernon Hills; Suzanne E. Radak, Wheeling, all of Ill.

[73] Assignee: G.D. Searle & Co., Skokie, Ill.

[21] Appl. No.: 373,329

[22] Filed: Apr. 30, 1982

Related U.S. Application Data

[62] Division of Ser. No. 241,984, Mar. 9, 1981, Pat. No. 4,356,302.

[51] Int. Cl.$^3$ ............................................ C07D 279/16
[52] U.S. Cl. ........................................ 544/51; 544/52
[58] Field of Search .................................... 544/51, 52

[56] References Cited

U.S. PATENT DOCUMENTS 3,635,956  1/1972  Krapcho .............................. 544/51
3,746,706  7/1973  Krapcho .............................. 544/51

OTHER PUBLICATIONS

Chorvat et al., *Chemical Abstracts*, vol. 98, Entry 72122n (1982).

Primary Examiner—John M. Ford
Attorney, Agent, or Firm—Albin J. Nelson; Albert Tockman

[57] ABSTRACT

4H-1,4 benzothiazine derivatives having anorectic activity and their preparation including intermediate compounds are disclosed.

11 Claims, No Drawings

4H-1,4-BENZOTHIAZINE DERIVATIVES AND INTERMEDIATES THERETO

This is a division of application Ser. No. 241,984, filed Mar. 9, 1981, now U.S. Pat. No. 4,356,302.

The present inventions relates to 4H-1,4 benzothiazine derivatives and novel intermediates used in the preparation thereof. More particularly, this invention provides chemical compounds of the formula

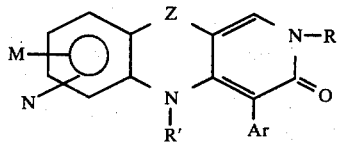

wherein R and R' each represent hydrogen or lower alkyl containing 1 to 4 carbon atoms; M and N represent hydrogen, halogen, nitro, amino, or alkoxy containing 1 to 4 carbon atoms; when M is other than alkoxy, N represents hydrogen and when M is an alkoxy group, N is hydrogen or the same alkoxy group; Z represents sulfur, sulfinyl or sulfonyl; Ar is phenyl, mono or di substituted phenyl, wherein the substituents may be halogen, hydroxy, trifluoromethyl, methoxy, cyano or lower alkyl having 1 to 4 carbon atoms; and pharmaceutically acceptable acid addition salts of the compounds of the above formula.

Among the substitutients represented by R and R' hydrogen is preferred. However, R and/or R' may represent lower alkyl, methyl, ethyl, 1-methyl ethyl, or propyl (i.e., alkyl containing less than 4 carbon atoms). Positioning of the substituents on the phenyl relative to the point of attachment of the phenyl, or where two are present, to each other is not critical. Thus, within the scope of this invention are o-, m-, or p-monosubstituted phenyls of the type described above, such as o-flourophenyl, o-chlorophenyl, m-trifluoromethylphenyl, p-bromophenyl and p-hydroxyphenyl and 2, 4-, 2,6-, and 3,4-disubstituted phenyls of the type described above, such as 2,4-dichlorophenyl, 2,6-dichlorophenyl and 3,4-dichlorophenyl. The preferred substituents of the substituted phenyl representing Ar are halogens.

The intermediates of this invention are represented by formula II

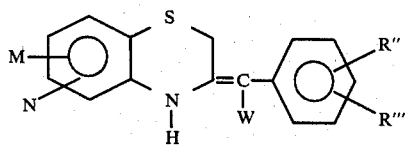

wherein W is CN, CONH$_2$ or CON=CHNXY, wherein X, and Y, are lower alkyl having 1 to 4 carbon atoms; and R'' represents hydrogen, methoxy, trifluoromethyl or lower alkyl having 1 to 4 carbon atoms when R''' is hydrogen, and when R'' is halogen, R''' is halogen or hydrogen.

Preferred acid addition salts of this invention are those which are pharmacologically acceptable, that is i.e., relatively non-toxic and effective for the purposes set forth here and below.

Equivalent to the foregoing compounds, including salts, for the purposes of this invention are solvates thereof in which pharmacologically insignificant amount of solvates are present.

The final product compounds to which this invention relate are useful because of their valuable pharmacological properties. Thus, for example, they are anorectic. The anorectic utility of the instant compounds is evident from results of a test showing a dose responsive decrease in food intake and subsequent weight loss upon administration of the compounds of the present invention. The procedure is as follows:

Male Sprague Dawley derived, COBS rats from Charles River Breeding Laboratories, (Portage, Mich.) weighed between 215 and 235 grams at the start of the experiment. All the animals were housed in individual cages and maintained on a 12 hour light-dark cycle with the light being on between 6 a.m. to 6 p.m. They were given access to powdered rat feed (Ralston Purina Rat Chow ® #5012) for only 4 hours a day from 10 a.m. to 2 p.m. Water was given at ad libitum. Food intake stabilized after about one week. On the eleventh day, the rats were divided into 4 groups of 13 rats each. The groups were matched for average food intake and body weight, based on the means of the previous 4 days.

Three of the groups were administered the compound in Example 39. Each group was assigned a specific dose. The doses were 5.6, 17.8 and 56.2 milligrams per kilogram of body weight. The compound was suspended in a normal saline vehicle (of which less than 1% of it contained a 50/50 mixture of propylene glycol and "TWEEN" ® 80). Concentrations of the compound were adjusted so that each rat received a volume of 2 milliliter per kilogram of body weight. The fourth group received 2 milliliter per kilogram of body weight of the vehicle only. The compound and vehicle preparations were given intraperitoneal one hour before the rats were given access to food.

Table 1 shows the results of the tests. A student t test was used for making statistical comparisons, and the p-values are based upon two-tailed comparisons.

TABLE 1

| Condition | | n | Mean Food Intake Grams (±S.D.) | Mean Weight Difference 24 hrs after compound administered Grams (±S.D.) |
|---|---|---|---|---|
| Normal Saline | | 13 | 21.2 (1.2) | +2.9[b] (4.6) |
| Compound — | 5.6 mg/kg | 13 | 17.4[a] (2.9) | −2.6[b] (3.8) |
| (Ex. 39) | 17.8 mg/kg | 13 | 16.5[a] (4.7) | −5.2[c] (5.1) |
| | 56.2 mg/kg | 13 | 12.1[a] (3.0) | −9.5[c] (2.9) |

[a] p < .002 compared with normal saline control group
[b] p < .05 between pre and post weight change
[c] p < .005 between pre and post weight change The compound prepared in accordance with the procedure of Example 39 produced a statistically significant dose responsive decrease in food intake when compared to the normal saline control groups. The drug groups showed a statistically significant (as compared with their previous day's weight) dose responsive weight loss after 24 hours, whereas the normal saline group gained an average of 2.9 grams. The compound produced a decrease in food intake and a subsequent loss in weight.

The anorectic utility of other compounds described herein can also be shown in the following procedure.

Six groups of 12 each male Sprague Dawley derived, COBS rats from Charles River Breeding Laboratories, (Portage, Mich.) were housed in individual cages, maintained on a 12 hour light-dark cycle with the light being on from 6 a.m. to 6 p.m. and given ad libitum access to water and rat feed (Ralston Purina Rat Chow ® #5001). Twenty-four hours prior to drug testing all food was removed from the cages. Groups of 12 rats each were matched on the basis of body weight. Forty-five minutes before they were again given access to food the rats were given, intraperitoneally, either one of the five experimental compounds or its vehicle (the control group). A single dose of 32 milligrams per kilogram of body weight of the compounds was administered. All animals received an injection volume of 2 milliliters per kilogram of body weight. The amount of food consumed after two hours of access to food was measured. The mean food intake for each test compound group is presented as a percentage of its vehicle control group in Table 2.

TABLE 2

| Compound Described in Example | Dose | N | Food Intake % of Control | Statistical Significance |
|---|---|---|---|---|
| 28 | 32 mg/kg | 12 | 51% | $p < .001$ |
| 29 | 32 mg/kg | 12 | 76% | $p = .06$ |
| 30 | 32 mg/kg | 12 | 61% | $p < .002$ |
| 33 | 32 mg/kg | 12 | 70% | $p < .02$ |
| 41 | 32 mg/kg | 12 | 53% | $p < .01$ |

Each of the given compounds of the present invention produced a decrease in food intake as compared with the control group. The p-values derived from statistical comparisons are presented in the last column. Only the results of the compound from Example 29 marginally missed the conventionally acceptable p-value of $p=0.05$. This could indicate that a somewhat higher dose of this compound would be required for a statistically significant reduction in food intake.

Compounds of formula II are useful as intermediates for the benzothiazine derivatives presently being disclosed and claimed.

Those skilled in the art will appreciate that the characterizing pharmacological responses to embodiments of this invention specified above are intended merely for purposes of illustration and, accordingly, are not to be construed as either delimiting or exclusionary.

For therapeutic purposes, the compounds of this invention are ordinarily combined with one or more adjuvants appropriate to the indicative route of administration. If per os, they may be mixed with lactose, sucrose, starch powder, cellulose esters of alkanoic acids, cellulose alkyl ethers, talc, stearic acid, magnesium stearate, magnesium oxide, sodium and calcium salts of phosphoric acid sulfuric acids, gelatin, acacia, sodium alginate, polyvinylpyrrolidone, and/or polyvinyl alcohol, and thus tableted or encapsulated for convenient administration; alternatively, they may be dissolved or suspended in water or a comparably innocuous liquid. Parenteral administration may be effected via sterile fluid and ad mixture with water, polyethylene glycol, propylene glycol, ethanol, corn oil, cottonseed oil, peanut oil, sesame oil, benzyl alcohol, sodium chloride and/or various buffers. Other adjuvants and modes of administration are well and widely known in the pharmaceutical arts; see for Example, F. W. Martin et al., "Remington's Pharmaceutical Sciences," 14th edition, Merck Publishing Co., Eaton, Penna., 1965.

Appropriate dosages in any given instance, of course, depend upon the nature and severity of the condition treated, the route of administration, and the species of mammal involved, including its size and any individual idiosyncrasies which obtained.

Compounds of this invention when M is not an amino group can be prepared as follows: a 2H-1,4-benzothiazin-3-(4H)-one of the formula

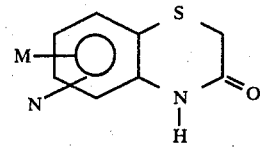

wherein M is hydrogen, halogen, nitro and/or alkoxy containing 1 to 4 carbon atoms and, when M is other than alkoxy, N is hydrogen, when M is alkoxy, N is hydrogen or the same alkoxy, is heated in 1,4-dioxane with diphosphorus pentasulfide to obtain a corresponding thione comprehended by the formula

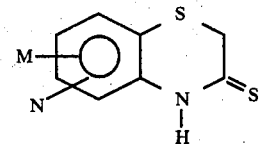

Such a thione is contacted with sodium hydride in tetrahydrofuran under nitrogen, and the resultant sodio derivative is contacted in situ with iodomethane to obtain a corresponding 3-methylthio-2H-1,4-benzothiazine comprehended by the formula

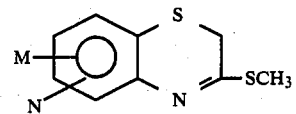

Such a methythio compound is heated in N,N-dimethylformamide under nitrogen with the sodio derivative of an optionally substituted 2-phenylacetonitrile prepared in situ by contacting the nitrile with sodium hydride, whereby a correspondingly optionally substituted 2-phenyl-2-[2,3-dihydro-4H-1,4-benzothiazin-3-ylidene]acetonitrile is obtained which is comprehended by the formula

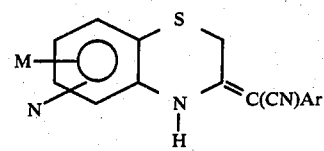

These nitriles are hydrolyzed in sulfuric acid/water solutions to afford the corresponding amides

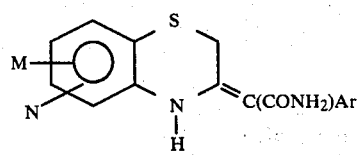

Such an amide is contacted in N,N-dimethylformamide under nitrogen with a dimethyl or diethyl ketal of the formula

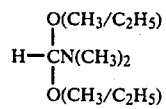

to give the corresponding adduct

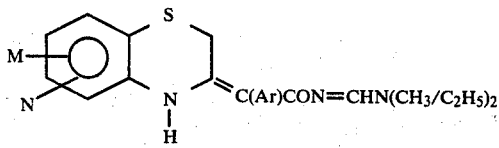

These adducts are converted to the corresponding tricyclic systems by two methods: method A, wherein intermediate compound A is treated with bis(dimethylamino)methoxy methane in DMF at 55 degrees to 60 degrees C. for 3 to 18 hours; method B, wherein the aforementioned adducts represented by intermediate compound A are converted to tricyclic pyrimidones by heating this adduct at 80 to 140 degrees centigrade

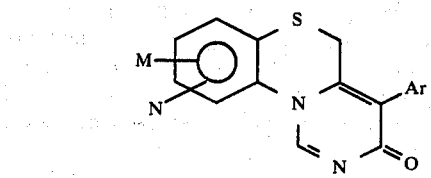

in DMF from 1 to 6 hours. These systems are treated with bis(dimethylamino)methoxymethane for 2 to 24 hours at 50 to 80 degrees centigrade and the resultant products

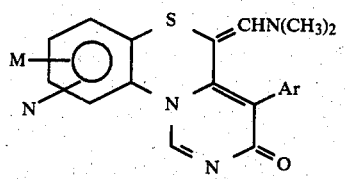

are then heated in aqueous DMF for 2 to 18 hours to afford the desired tricyclic pyridones

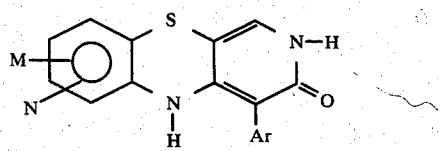

A 4-phenyl-5H-pyrido[3,4-b][1,4]benzothiazin-3(2H)-one of the formula

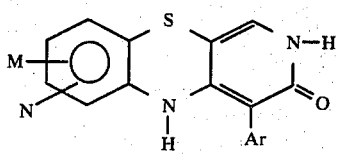

wherein M=N=H
is contacted in N,N-dimethylformamide with an iodoalkane, in the presence of potassium carbonate to obtain a corresponding 2-alkyl-4-phenyl-5H-pyrido[3,4-b][1,4]benzothiazin-3(2H)-one comprehended by the formula

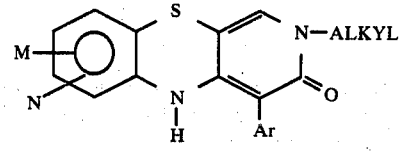

and which in turn is heated in N,N-dimethylformamide with an iodoalkane in the presence of potassium carbonate to obtain a corresponding 2,5-dialkyl-4-phenyl-5H-pyrido[3,4-b][1,4]benzothiazin 3(2H)-one comprehended by the formula

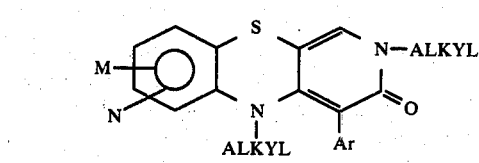

Such a 2,5 dialkyl-4-phenyl-5H-pyrido[3,4-b][1,4]benzothiazin-3(2H)-one is contacted with ethaneperoxoic acid in acetic acid to obtain a 10-oxide comprehended by the formula

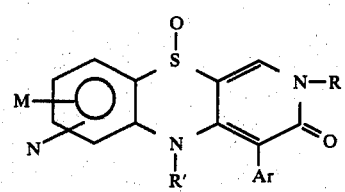

and such a 10-oxide or its immediate precursor is heated with ethaneperoxoic acid in acetic acid to obtain a corresponding 10,10-dioxide comprehended by the formula

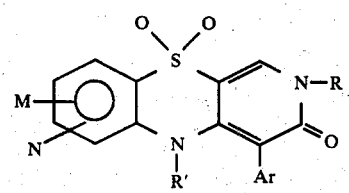

Alternatively, a 4-phenyl-5H-pyrido[3,4-b][1,4]benzothiazin-3(2H)-one of the formula

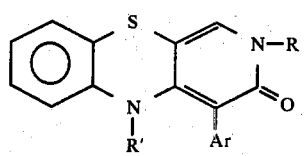

is (1) heated with bromine in a mixture of carbon tetrachloride and acetic acid to obtain a corresponding 8-bromo compound comprehended by the formula

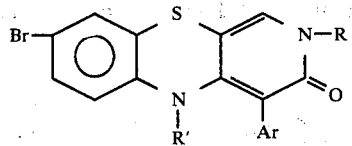

or (2) contacted with a cold mixture of nitric and sulfuric acids to obtain a corresponding 8-nitro 10-oxide comprehended by the formula

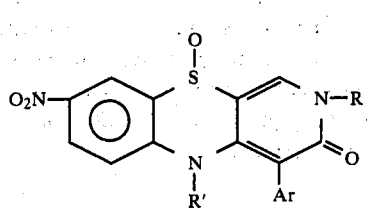

which in turn is (1) heated with triphenylphosphine in a mixture of tetrachloromethane and acetonitrile to obtain a corresponding 10-desoxidic compound comprehended by the formula

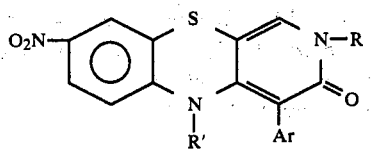

and (2) heated with stannous chloride dihydrate in a mixture of hydrochloric and acetic acids to obtain—upon neutralization—a corresponding 8-amino 10-desoxidic compound comprehended by the formula

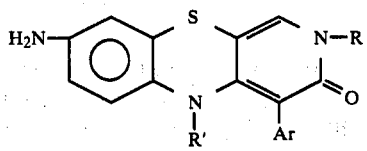

Finally, an acid addition salt of the invention is obtained by contacting—ordinarily in a solvent medium—an amino compound of the preceding formula with an inorganic or strong organic acid such as hydrochloric, hydrobromic, hydriodic, nitric, phosphoric, sulfuric or the methyl or ethyl ester thereof, sulfamic, benzenesulfonic, methylbenzenesulfonic, acetic, 2-hydroxypropanoic, 3-phenyl-2-propanoic, butanedioic, 2,3-dihydroxy-butanedioic, 2-butenedioic, 2-hydroxy-1,2,3-propanetricarboxylic, gluconic, ascorbic, benzoic, or the like, the relative amount of amino compound contacted being determined by the basicity of the acid and the stoichiometry elected where options are presented. Those substituted phenyl acetonitriles which are appropriate for Method A may include but should not be limited to:

p-chlorophenylacetonitrile, o-chlorophenylacetonitrile, o-fluorophenylacetonitrile, m-trifluoromethylphenyl acetonitrile, phenylacetonitrile. Those substituted phenylacetonitriles appropriate for Method B may include but should not be limited to p-bromophenylacetonitrile, p-fluorophenylacetonitrile, p-methoxyphenylacetonitrile.

Use of the appropriately substituted 2H-1,4-benzothiazin-3-(4H)-one such as those halogenated at the 5, 6, or 7-position, or the 5-nitro derivative or the 6,7-dimethoxy derivative in the previously described sequence and various substituted phenylacetonitriles as described will produce the desired pyridones with this corresponding substitution patterns on both the fused aromatic ring and the phenyl substitutent of the pyridone ring.

In addition use of various disubstituted phenylacetonitriles such as 3,4-dichloro- or 2,6-dichloro- or 2,4-dichloro- for the monosubstituted phenylacetonitriles in either Method A or Method B will result in disubstituted phenyl groups on the pyridone ring. The fused aromatic ring of these tricycles pyridones may be unsubstituted, mono- or disubstituted.

Throughout the foregoing preparative disclosure, R, R', R'', R''', M, N, X, Y, and Z retain the meanings originally assigned.

The following examples describe in detail compounds illustrative of the present invention and methods which have been devised for their preparation. It will be apparent to those skilled in the art that many modifications, both of materials and of methods, may be practiced without departing from the purpose and intent of this disclosure. Throughout the examples hereinafter set forth, temperatures are given in degrees Centigrade and relative amounts of materials in part by weight, except as otherwise noted.

EXAMPLE 1

In a one liter flask is placed 10.8 parts of prewashed sodium hydride in 150 parts of N,N-dimethyl-formamide (DMF) at room temperature. After stirring for five minutes under nitrogen atmosphere, 30 parts of 2H-1,4-benzothiazine-3(4H)-thione[J. Med. Chem., 12, 290(1969)] is added in portions over a period of 30 minutes and continuously stirred at room temperature for 20 minutes. To the reaction mixture is then added 15 parts of methyl iodide and the mixture stirred at room temperature for 20 minutes under nitrogen. Removal of solvent by vacuum distillation under nitrogen affords 3-methylthio-2H-1,4-benzothiazine as the residue. Since the product is subject to spontaneous hydrolytic decomposition, it is not usually isolated for the purposes of this invention but instead employed as the solution in DMF preparable via the foregoing procedure.

EXAMPLE 2

A mixture of 12 parts 50% sodium hydride/mineral oil dispersion previously washed with hexane to remove the oil is suspended in 300 ml of DMF under a nitrogen atmosphere and is treated with 32 parts of p-chlorophenylacetonitrile. After the mixture is stirred at room temperature for 15 minutes to 2 hours, 30 parts of 3-methylthio-2H-1,4-benzothiazine from Example 1 is added to the mixture and the reaction mixture stirred at room temperature for one hour.

The mixture is neutralized with acetic acid and diluted with one to two volumes of water. The mixture is stirred at room temperature for 30 minutes during which time the product which precipitated from the reaction mixture is filtered and dried to yield (2H-1,4-benzothiazin-3(4H)-ylidene)(4-chlorophenyl)acetonitrile melting at approximately 137°–139°.

EXAMPLE 3

Substitution of 32 parts of o-flurophenylacetonitrile for the 32 parts of p-chlorophenylacetonitrile in Example 2 affords by the procedure therein detailed, (2H-1,4-benzothiazin-3(4H)-ylidene)(2-fluorophenyl)acetonitrile.

EXAMPLE 4

Substitution of 32 parts of o-chlorophenylacetonitrile for 32 parts of p-chlorophenylacetonitrile in Example 2 affords, by the procedure therein detailed, (2H-1,4-benzothiazin-3(4H)-ylidene)(2-chlorophenyl)acetonitrile melting at about 155°–158°.

EXAMPLE 5

Substitution of 32 parts of m-trifluoromethylphenylacetonitrile for 32 parts of p-chlorophenylacetonitrile called for in Example 2 affords, by the procedure therein detailed, (2H-1,4-benzothiazin-3(4H)-ylidene [3-(trifluoromethyl)phenyl]acetonitrile melting in the range of 142°–145°.

EXAMPLE 6

Substitution of 32 parts of phenylacetonitrile for 32 parts of p-chlorophenylacetonitrile in Example 2 affords, by the procedure therein described, (2H-1,4-benzothiazin-3(4H)-ylidene)phenylacetonitrile.

EXAMPLE 7

Substitution of 32 parts of either o-methylphenylacetonitrile, m-methylphenylacetonitrile, or p-methylphenylacetonitrile for 32 parts of p-chlorophenylacetonitrile in Example 2 affords, by the procedure therein described respectively, (2H-1,4-benzothiazin-3(4H)-ylidene)(2-methylphenyl)acetonitrile, (2H-1,4-benzothiazin-3(4H)-ylidene)(3-methylphenyl)acetonitrile and (2H-1,4-benzothiazin-3(4H)-ylidene)(4-methylphenyl)acetonitrile.

EXAMPLE 8

A mixture of 30 parts of (2H-1,4-benzothiazin-3(4H)-ylidene)(4-chlorophenyl)acetonitrile, 180 parts concentrated sulfuric acid and 18 parts water is stirred at room temperature for 1½ hours. The mixture is cooled to 0°–5° and diluted with 1 to 2 volumes of water which results in a crystalline solid which is filtered, dried and crystallized from methanol to afford crystalline 2-(2H-1,4-benzothiazin-3(4H)-ylidene)-2-(4-chlorophenyl)acetamide melting at about 188°–191°.

EXAMPLE 9

Substitution of 30 parts of (2H-1,4-benzothiazin-3-(4H-ylidene)phenyl acetonitrile for 30 parts of (2H-1,4-benzothiazin-3(4H)-ylidene)(4-chlorophenyl) acetonitrile in Example 8 affords, by the procedure therein described, 2-(2H-1,4-benzothiazin-3(4H)-ylidene)-2-phenylacetamide melting at about 149°–151°.

EXAMPLE 10

Substitution of 30 parts of (2H-1,4-benzothiazin-3(4H)-ylidene)(2-chlorophenyl)acetonitrile for 30 parts of (2H-1,4-benzothiazin-3(4H)-ylidene)(4chlorophenyl)acetonitrile in Example 8 affords, by the procedure therein described, 2-(2H-1,4-benzothiazin-3(4H)-ylidene-2-(2-chlorophenyl)acetamide melting in the range of 167°–169°.

EXAMPLE 11

Substitution of 30 parts of (2H-1,4-benzothiazin-3(4H)-ylidene)(3-trifluoromethylphenyl)acetonitrile for 30 parts of (2H-1,4-benzothiazin-3(4H)-ylidene(4-chlorophenyl)acetonitrile in Example 8 affords, by the procedure therein described, 2-(2H-1,4-benzothiazin-3(4H)-ylidene)-2-[3-(trifluoromethyl)phenyl]acetamide melting in the range of 167°–168°.

EXAMPLE 12

Substitution of 30 parts of 2H-1,4-benzothiazin-3(4H)-ylidene)(2fluorophenyl)acetonitrile for 30 parts of (2H-1,4-benzothiazin-3(4H)-ylidene)(4 chlorophenyl)acetonitrile in Example 8 affords, by the procedure therein described, 2-(2H-1,4-benzothiazin-3(4H)-ylidene-2-(2-fluorophenyl)acetamide melting in the range of 156°–158°.

EXAMPLE 13

Substitution of 30 parts of either 2H-1,4-benzothiazin-3(4H)-ylidene(2-methylphenyl) acetonitrile, 2H-1,4-benzothiazin-3(4H)-ylidene(3-methylphenyl)acetonitrile or 2H-1,4-benzothiazin-3(4H)-ylidene(4-methylphenyl)acetonitrile in Example 8 affords, by the procedure therein described respectively, 2-(2H-1,4-benzothiazin-3(4H)-ylidene-2-(2-methylphenyl)acetamide, 2-(2H-1,4-benzothiazin-3(4H)-ylidene-2-(3-methylphenyl)acetamide and 2-(2H-1,4-benzothiazin-3(4H)-ylidene-2-(4-methylphenyl)acetamide.

EXAMPLE 14 (METHOD A)

In a one liter flask equipped with a magnetic stirrer are placed 35 parts of 2-(2H-1,4-benzothiazin-3(4H)-ylidene-2-(4-chlorophenyl)acetamide, 300 parts of DMF and 20 parts of dimethylformamide diethyl acetal reagent. The mixture is stirred at room temperature overnight, and 42 parts of methoxy(dimethylamino)methane is then added. The mixture is heated to 50° for six hours, cooled to room temperature, and poured onto about 400 parts of water and stirred at room temperature. The oily semi-solid which formed is collected, triturated with methanol, filtered and dried.

The yellow material is further triturated with about 500 parts of methanol with heating then cooled, and the solid is collected, washed with ethyl acetate followed by ether and dried. The yellow crystalline solid is recrystallized from aqueous DMF to yield 4-(4-chlorophenyl)-5H-pyrido[3,4-b][1,4]benzothiazin-3(2H)-one which melts above 330°.

EXAMPLE 15

Substitution of 35 parts of 2-(2H-1,4-benzothiazin-3(4H)-ylidene-2-(phenyl)acetamide called for in Example 14 affords, by the procedure there detailed, 4-phenyl-5H-pyrido[3,4-b][1,4]benzothiazin-3(2H)-one melting at about 266°–271°.

EXAMPLE 16

Substitution of 35 parts of 2-(2H-1,4-benzothiazin-3(4H)-ylidene-2-(2-chlorophenyl) acetamide called for in Example 14 affords, by the procedure there detailed, 4-(2-chlorophenyl)-5H-pyrido[3,4-b][1,4]benzothiazin-3(2H)-one melting at about 320°–323°.

EXAMPLE 17

Substitution of 35 parts of 2-(2H-1,4-benzothiazin-3(4H)-ylidene-2-[3-(trifluoromethyl)phenyl]acetamide called for in Example 14 affords, by the procedure therein described, 4-[(3-trifluoromethyl)phenyl]-5H-pyrido[3,4-b][1,4]benzothiazin-3(2H)-one melting at about 268°–270° C.

EXAMPLE 18

Substitution of 35 parts of 2-(2H-1,4-benzothiazin-3(4H)-ylidene-2-(2-fluorophenyl)acetamide called for in Example 14 affords, by the procedure therein described, 4-(2-fluorophenyl)-5H-pyrido[3,4-b][1,4]benzothiazin-3(2H)-one, which melts above 300°.

EXAMPLE 19

Substitution of 35 parts of either 2-(2H-1,4-benzothiazin-3(4H)-ylidene-2-(2-methylphenyl)acetamide, 2-(2H-1,4-benzothiazin-3(4H)-ylidene-2-(3-methylphenyl)acetamide or 2-(2H-1,4-benzothiazin-3(4H)-ylidene-2-(4 methylphenyl)acetamide called for in Example 15 affords by the procedure therein detailed respectively 4-(2-methylphenyl)-5H-pyrido[3,4-b][1,4]benzothiazin-3(2H)-one, 4-(3-methylphenyl-5H-pyrido[3,4-b][1,4]benzothiazin-3(2H)-one and 4-(4-methylphenyl)-pyrido[3,4-b][1,4]benzothiazin-3(2H)one.

EXAMPLE 20

Substitution of 32 parts of p-fluorophenylacetonitrile for the 32 parts of p-chlorophenylacetonitrile in example 2 affords by the procedure therein detailed (2H-1,4-benzothiazin-3(4H)-ylidene)(4-fluorophenyl)acetonitrile melting at about 120°–122° C.

EXAMPLE 21

Substitution of 32 parts of p-methoxyphenylacetonitrile for the 32 parts of p-chlorophenylacetonitrile in example 2 affords by the procedure therein described (2H-1,4-benzothiazin-3(4H)-ylidene)(4-methoxyphenyl)acetonitrile melting at about 151°–153° C.

EXAMPLE 22

Substitution of 32 parts of p-bromophenylacetonitrile for the 32 parts of p-chlorophenylacetonitrile in example 2 affords by the procedure therein described (2H-1,4-benzothiazin-3(4H)-ylidene)(4-bromophenyl)acetonitrile melting at about 155°–157° C.

EXAMPLE 23

Substitution of 32 parts of either 3,4-dichlorophenylacetonitrile, 2,4-dichlorophenylacetonitrile or 2,6-dichlorophenylacetonitrile in Example 2 affords by the procedure therein described respectively (2H-1,4-benzothiazin-3(4H)-ylidene)(3,4-dichlorophenyl)acetonitrile, (2H-1,4-benzothiazin-3(4H)-ylidene)(2,4-dichlorophenyl)acetonitrile, or (2H-1,4-benzothiazin-3(4H)-ylidene)(2,6-dichlorophenyl)acetonitrile.

EXAMPLE 24

Substitution of 30 parts of (2H-1,4-benzothiazin-3(4H)-ylidene)(4-fluorophenyl)acetonitrile for the 30 parts of substrate of example 8 affords by the procedure therein described 2-(2H-1,4-benzothiazin-3(4H)-ylidene)-2-(4-fluorophenyl)acetamide melting at about 190°–192° C.

EXAMPLE 25

Substitution of 30 parts of (2H-1,4-benzothiazin-3(4H)-ylidene)(4-methoxyphenyl)acetonitrile for the 30 parts of substrate of Example 8 affords by the procedure therein described 2-(2H-1,4-benzothiazin-3(4H)-ylidene)-2-(4-methoxyphenyl)acetamide melting at about 183°–184° C.

EXAMPLE 26

Substitution of 30 parts of (2H-1,4-benzothiazin-3(4H)-ylidene)(4-bromophenyl)acetonitrile for the 30 parts of substrate of example 8 affords by the procedure therein described 2-(2H-1,4-benzothiazin-3(4H)-ylidene)-2-(4-bromophenyl)acetamide melting at about 209°–210° C.

EXAMPLE 27

Substitution of 30 parts of either (2H-1,4-benzothiazin-3(4H)-ylidene)(3,4-dichlorophenyl)acetonitrile, (2H-1),4-benzothiazin-3(4H)-ylidene)(2,4-dichlorophenyl)acetonitrile, or (2H-1,4-benzothiazin-3(4H)-ylidene)(2,6-dichlorophenyl)acetonitrile for the substrates of example 8 affords by the procedure therein described respectively 2-(2H-1,4-benzothiazin-3(4H)-ylidene)-2-(3,4-dichlorophenyl)acetamide, 2-(2H-1,4-benzothiazin-3(4H)-ylidene)-2-(2,4-dichlorophenyl)acetamide and 2-(2H-1,4-benzothiazin-3(4H)-ylidene)-2-(2,6-dichlorophenyl acetamide.

EXAMPLE 28 (METHOD B)

To 4 parts of 2-(2H-1,4-benzothiazin-3(4H)-ylidene)-2-(4-fluorophenyl)acetamide in 80 parts of DMF is added 6 parts dimethylformamide diethyl acetal and the reaction mixture was stirred at room temperature for 2 to 6 hours then heated at 80°–140° C. for 1 to 6 hours. After cooling 6 parts of methoxy-bis-(dimethylamino)methane is added and the reaction mixture then heated at 50° to 80° C. for 2 to 24 hrs. The cooled reaction mixture is then diluted with 40 parts of water and refluxed for 2 to 18 hr. Upon cooling the precipitate present was collected and recrystallized from aqueous DMF to give 4-(4-fluorophenyl)-5H-pyrido[3,4-b][1,4]benzothiazin-3(2H)-one which melts above 300°.

EXAMPLE 29

Substitution of 4 parts of 2-(2H-1,4-benzothiazin-3(4H)-ylidene)-2-(4-methoxyphenyl)acetamide for the substrate in example 28 affords by the procedure therein described 4-(4-methoxyphenyl)-5H-pyrido[3,4-b][1,4]benzothiazin-3(2H)one melting above 300° C.

EXAMPLE 30

Substitution of 4 parts of 2-(2H-1,4-benzothiazin-3(4H)-ylidene)-2-(4-bromophenyl)acetamide for the substrate of example 28 affords by the procedure therein described 4-(4-bromophenyl)-5H-pyrido[3,4-b][1,4]benzothiazin-3(2H)-one melting above 300° C.

EXAMPLE 31

Substitution of 4 parts of either 2-(2H-1,4-benzothiazin-3(4H)-ylidene)-2-(3,4-dichlorophenyl)acetamide, 2-(2H-1,4-benzothiazin-3(4H)-ylidene)-2-(2,4-dichlorophenyl)acetamide or 2-(2H-1,4-benzothiazin-3(4H)-ylidene)-2-(2,6-dichlorophenyl)acetamide for the substrate of example 28 affords by the procedure therein described respectively 4-(3,4-dichlorophenyl)-5H-pyrido[3,4-b][1,4]benzothiazin-3(2H)-one, 4-(2,4-dichlorophenyl)-5H-[3,4-b][1,4]benzothiazin-3(2H)-one and 4-(2,6-dichlorophenyl)-5H-pyrido[3,4-b][1,4]benzothiazin-3-(2H)-one.

EXAMPLE 32

To 10 parts of 4-(4-bromophenyl)-5H-pyrido[3,4-b][1,4]benzothiazin-3(2H)-one suspended in 300 parts of DMF is added 4 parts of cuprous cyanide and the reaction mixture is refluxed for 2 to 12 hours. After cooling, water is added and the solution extracted with ethyl acetate. The combined extracts are washed with saturated NaCl solution and dried. Solvent removal gives a residue which upon recrystallization from aqueous DMF gives 4-(4-cyanophenyl)-5H-pyrido[3,4-b][1,4]benzothiazin-3(2H)-one, which melts above 290° C.

EXAMPLE 33

To 10 parts pyridine hydrochloride heated to 170° under a stream of nitrogen is added 0.5 parts of 4-(4-methoxyphenyl)-5H-pyrido[3,4-b][1,4]benzothiazin-3(2H)-one in one portion. The reaction mixture is refluxed for 45 minutes, cooled, water is added and the solid which forms is collected and dried to yield 4-(4-hydroxyphenyl)-5H-pyrido[3,4-b][1,4]benzothiazin-3(2H)-one, m.p. greater than 300°.

EXAMPLE 34

To 3 parts of the product of the process described in Example 14, 4-(4-chlorophenyl)-5H-pyrido[3,4-b][1,4]benzothiazin-3(2H)-one, suspended in 5 parts acetic acid is added and 1 part 40% peracetic acid. After ten minutes reaction time, water is added to the now homogeneous reaction mixture and the precipitate which forms is collected and recrystallized from aqueous DMF to yield white needles of 4-(4-chlorophenyl)-5H-pyrido[3,4-b][1,4]benzothiazin-3(2H)-one 10 oxide, melting above 310°.

EXAMPLE 35

Substitution of the products from examples 15, 16, 17, 18, 19, 28, 29, 30, 31, 32 and 33 for the 4-(4-chlorophenyl)-5H-pyrido[3,4b-][1,4]benzothiazin-3(2H)-one in example 34 affords the corresponding 4-(aryl)-5H-pyrido[3,4-b][1,4]benzothiazin-3(2H)-one 10 oxide.

EXAMPLE 36

A mixture of 1 part of 4-(4-chlorophenyl)-5H-pyrido[3,4-b][1,4]benzothiazin-3(2H)-one, 10 parts of ethaneperpoxoic acid, and 10 parts of glacial acetic acid is stirred and heated at 25° to 60° for 1 to 20 hours, whereupon insoluble solids are filtered, washed with ethyl acetate, and dried in vacuo at 110° to give 4-(4-chlorophenyl)-5H-pyrido[3,4-b][1,4]benzothiazin-3(2H)-one 10,10-dioxide melting above 300°.

EXAMPLE 37

Substitution of the products from example 35 for the starting material in example 36 will give the corresponding 4-(aryl)-5H-pyrido[3,4-b][1,4]benzothiazin-3(2H)-one 10,10-dioxide.

EXAMPLE 38

Substitution of the corresponding substituted 2H-1,4 benzothiazine-3(4H)-thione, derived from the appropriate 2H-1, 4-benzothiazin-3(4H)-ones such as the 5-chloro-derivative [J. Chem. Soc., 893 (1945)] or the 6-chloro-derivative [Can. J. Chem., 44, 1733 (1965)] or the 7-chloro-derivative [Can. J. Chem., 48, 1859 (1970)] or the 6-fluoro-derivative [J. Chem. Soc., 787 (1952)] or the 6-bromo-derivative [J. Chem. Soc., 2624 (1957)] or the 5-nitro-derivative [Ann. Chem. (Rome) 588, 1226 (1968)] or the 6,7 dimethoxy derivative [J. Proc. Roy. Soc., N.S. Wales, 71, 112 (1938)] according to the procedure described in J. Med. Chem., 12, 290 (1969), in example 1 will afford the corresponding 3-methylthio derivatives. These in turn when substituted in examples 2, 3, 4, 5, 6, 7, 20, 21, 22 or 23 will give the corresponding acetonitrile derivatives. These turn when treated with aqueous sulfuric acid as described in example 8, 9, 10, 11, 12, 13, 24, 25, 26, or 27 will give the corresponding acetamide derivatives. These in turn when treated with DMF diethyl acetal then methoxy bis(dimethylamino)methane as described in examples 14 thru 19 will give the corresponding 4-(4-chlorophenyl)-5H-pyrido[3,4-b][1,4]benzothiazin-3(2H)-one or 4-phenyl-5H-pyrido[3,4-b][1,4]benzothiazin-3(2H)-one or 4-(2-chlorophenyl)-5H-pyrido[3,4-b][1,4]benzothiazin-3(2-H)-one or 4-(3-trifluoromethylphenyl)-5H-pyrido[3,4-b][1,4]benzothiazin-3(2H)-one or 4(2-fluorophenyl)-5H-pyrido[3,4-b][1,4]benzothiazin-3(2H)-one with the respective substitution on the benzene ring. Alternatively, when these acetamides are treated with DMF diethyl acetal, methoxy bis(dimethylamino)methane and water as described in examples 28 thru 31, they will give the corresponding 4-(4-fluorophenyl)-5H-pyrido[3,4-b][1,4]benzothiazin-3(2H)-one or 4-(4-methoxyphenyl)-5H-pyrido[3,4-b][1,4]benzothiazin-3(2H)-one or 4(4-bromophenyl)-5H-pyrido[3,4-b][1,4]benzothiazin-3(2H)-one with the respective substituents on the benzene ring.

EXAMPLE 39

To a solution of 1 part 4-(4-chlorophenyl)-5H-pyrido[3,4-b][1,4]benzothiazin-3(2H)-one in 25 parts of concentrated hydrochloric acid is added 25 parts methanol. The solution is warmed to the mean boiling point of the alcohol. Another 50 parts of methanol is added and heating continued until nearly all the solid material is dissolved. The hot solution is filtered to remove undissolved solids and upon concentrating the solution volume of filtrate in a suction flask, yellow needles of 4-(4-chlorophenyl)-5H-pyrido[3,4-b][1,4]benzothiazin-3-ol hydrochloride result, melting above 300° C.

EXAMPLE 40

Substitution of the products from examples 15, 16, 17, 18, 19, 28, 29, 30, 31, 32 and 33 for the 4-(4-chlorophenyl)-5H-pyrido[3,4-b][1,4]benzothiazin-3(2H)one, in example 39 affords the corresponding 4-(aryl)-5H-pyrido[3,4-b][1,4]benzothiazin-3-ol hydrochlorides.

EXAMPLE 41

To a solution of 1 part of 4-[(3-trifluoromethyl)-phenyl]-5H-pyrido[3,4b][1,4]benzothiazin-3(2H)-one in 20 parts hydrochloric acid is added 60 parts methanol in 10 parts portions with swirling and heating on a steam bath. Near the boiling point of the alcohol, the hot solution is filtered through a scintered glass funnel. Then the filtrate is concentrated with vacuum while keeping the liquid warm. After 3 portions of hydrochloric acid, the liquid is essentially finished crystallizing as short, fluffy needles. These are collected, washed, dried in air and ground using mortar and pestle to a flour consistency to yield 4-[(3-trifluoromethyl)phenyl]-5H-pyrido[3,4-b][1,4]benzothiazin-3-ol, hydrochloride as a yellow powder.

EXAMPLE 42

To 0.5 parts 4-(2-chlorophenyl)-5H-pyrido[3,4-b][1,4]benzothiazin-3(2H)-one suspended in 10 parts concentrated hydrochloric acid is added 10 parts methanol while gently warming the solution on a steam bath. A brown gum is formed and the second 10 part portion of methanol is added to substantially solubilize the gum. Near the boiling point of the alcohol, the solution is filtered. The filtrate is concentrated on a steam bath using a nitrogen stream. A gold precipitate formed which was air dried and pulverized to yield a bright yellow powder, 4-(2-chlorophenyl)-5H-pyrido[3,4-b][1,]benzothiazin-3-ol, hydrochloride.

EXAMPLE 43

Substitution of 0.25 parts of 4-(2-fluorophenyl)-5H-pyrido[3,4-b][1,4]benzothiazin-3(2H)-one for the 4-(2-chlorophenyl)-5H-pyrido[3,4-b][1,4]benzothiazin-3(2H)-one called for in example 42, using 10 parts concentrated hydrochloric acid with 25 parts methanol, affords by the procedure detailed therein 4-(2-fluorophenyl)-5H-pyrido[3,4-b][1,4]benzothiazin-3-ol, hydrochloride.

What is claimed is:

1. An intermediate compound of the formula

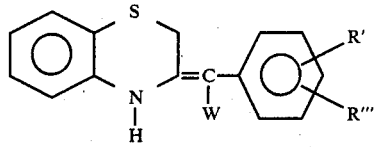

wherein W represents CN, CONH₂ or CON=CHNXY, wherein X represents a lower alkyl of 1 to 4 carbon atoms and Y represents a lower alkyl of 1 to 4 carbon atoms; and R" represents hydrogen, methoxy, trifluoromethyl or lower alkyl having 1 to 4 carbon atoms when R'" represents hydrogen, and when R" represents halogen, R'" represents hydrogen or halogen.

2. A compound according to claim 1 wherein W is CN.
3. A compound according to claim 2 wherein R'" is hydrogen.
4. A compound according to claim 2 wherein R'" is halogen.
5. A compound according to claim 1 wherein W is CONH₂.
6. A compound according to claim 5 wherein R'" is hydrogen.
7. A compound according to claim 5 wherein R'" is halogen.
8. A compound according to claim 1 wherein W is CON=CHNXY.
9. A compound according to claim 8 wherein X is CH₃ and Y is CH₃.
10. A compound according to claim 8 wherein R'" is hydrogen.
11. A compound according to claim 8 wherein R'" is halogen.

* * * * *

United States Patent and Trademark Office
CERTIFICATE OF CORRECTION

PATENT NO. : 4,399,279
DATED : August 16, 1983
INVENTOR(S) : Robert J. Chorvat, et al It is certified that error appears in the above-identified patent and that said Letters Patent are hereby corrected as shown below:

The correct structure for Claim 1 is:

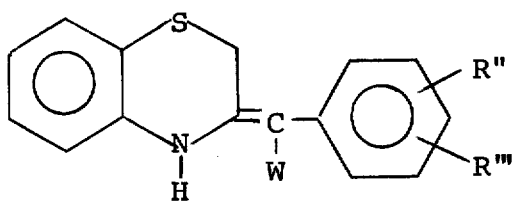

Signed and Sealed this

Twenty-eighth Day of February 1984

[SEAL]

Attest:

GERALD J. MOSSINGHOFF

Attesting Officer    Commissioner of Patents and Trademarks